(12) United States Patent
Lin

(10) Patent No.: US 11,712,373 B2
(45) Date of Patent: Aug. 1, 2023

(54) WOUND THERAPY APPARATUS WITH SCAR MODULATION PROPERTIES AND RELATED METHODS

(71) Applicant: Edward D. Lin, Osprey, FL (US)

(72) Inventor: Edward D. Lin, Osprey, FL (US)

(*) Notice: Subject to any disclaimer, the term of this patent is extended or adjusted under 35 U.S.C. 154(b) by 345 days.

(21) Appl. No.: 15/663,714

(22) Filed: Jul. 29, 2017

(65) Prior Publication Data

US 2019/0029886 A1 Jan. 31, 2019

(51) Int. Cl.
*A61F 13/02* (2006.01)
*A61F 13/00* (2006.01)
(Continued)

(52) U.S. Cl.
CPC ...... *A61F 13/0206* (2013.01); *A61B 5/14539* (2013.01); *A61B 5/4839* (2013.01);
(Continued)

(58) Field of Classification Search
CPC .............. A61F 13/0206; A61F 13/0256; A61F 13/00063; A61F 2013/0028;
(Continued)

(56) References Cited

U.S. PATENT DOCUMENTS 2,280,915 A 4/1942 Johnson
3,026,874 A 3/1962 Stevens
(Continued)

FOREIGN PATENT DOCUMENTS

CH 201010139947.2 1/2016
CN 102008373 A 4/2011
(Continued)

OTHER PUBLICATIONS

International Search Report for International Application No. PCT/US2018/043953 dated Oct. 9, 2018.
(Continued)

*Primary Examiner* — Benjamin J Klein
*Assistant Examiner* — Ilya Y Treyger
(74) *Attorney, Agent, or Firm* — Cardle Patent Law Chtd

(57) ABSTRACT

A wound therapy apparatus is disclosed herein. In various aspects, the wound therapy apparatus may include a distal layer to contact a wound bed, the distal layer comprised of silicone, and fenestrations disposed about the distal layer pass between a distal side of the distal layer and a proximal side of the distal layer to communicate between the distal side and the proximal side. A pad may cooperate with the proximal side of the distal layer to receive exudate communicated through the distal layer from the wound bed via the fenestrations, in various aspects. Various materials including medicament(s) may be communicated to the wound bed through the distal layer via the fenestrations, in various aspects. A structural member may be included in various aspects to secure the distal layer and pad to a skin surface, in various aspects. Methods of use of the wound therapy apparatus are disclosed herein. This Abstract is presented to meet requirements of 37 C.F.R. § 1.72(b) only, and is not intended to identify key elements of the apparatus, methods, and compositions of matter disclosed herein or to delineate the scope thereof.

20 Claims, 6 Drawing Sheets

(51) Int. Cl.
  *A61L 15/58* (2006.01)
  *A61L 15/44* (2006.01)
  *A61L 15/26* (2006.01)
  *A61B 5/145* (2006.01)
  *A61L 15/42* (2006.01)
  *A61B 5/00* (2006.01)
  *A61M 1/00* (2006.01)

(52) U.S. Cl.
  CPC ...... *A61B 5/6833* (2013.01); *A61F 13/00063* (2013.01); *A61F 13/0256* (2013.01); *A61L 15/26* (2013.01); *A61L 15/425* (2013.01); *A61L 15/44* (2013.01); *A61L 15/58* (2013.01); *A61B 5/445* (2013.01); *A61B 5/4842* (2013.01); *A61F 2013/0028* (2013.01); *A61F 2013/00119* (2013.01); *A61L 2420/02* (2013.01); *A61L 2420/06* (2013.01); *A61M 1/90* (2021.05)

(58) Field of Classification Search
  CPC ....... A61F 2013/00119; A61B 5/14539; A61B 5/4839; A61B 5/6833; A61B 5/4842; A61B 5/445; A61L 15/58; A61L 15/44; A61L 15/26; A61L 2420/06; A61L 2420/02; A61L 15/425; A61M 1/0088
  See application file for complete search history.

(56) References Cited

U.S. PATENT DOCUMENTS

| | | | |
|---|---|---|---|
| 3,300,786 A | 1/1967 | Rosenvold et al. | |
| 4,163,822 A * | 8/1979 | Walter | A61L 15/48 428/317.3 |
| 4,328,799 A | 5/1982 | LoPiano | |
| 4,399,816 A * | 8/1983 | Spangler | A61F 13/0206 128/888 |
| 4,635,618 A | 1/1987 | Munz | |
| 5,086,763 A | 2/1992 | Hathman | |
| 5,154,697 A | 10/1992 | Loori | |
| D364,679 S | 11/1995 | Heaton et al. | |
| 5,522,794 A * | 6/1996 | Ewall | A61F 13/023 602/41 |
| 5,562,107 A | 10/1996 | Lavender et al. | |
| 5,607,388 A * | 3/1997 | Ewall | A61F 13/023 602/46 |
| 5,636,643 A | 6/1997 | Argenta et al. | |
| 5,667,502 A | 9/1997 | Holtermann | |
| 5,769,806 A | 6/1998 | Radow | |
| 5,792,090 A | 8/1998 | Ladin | |
| 5,899,207 A | 5/1999 | Scheinberg | |
| 5,980,497 A | 11/1999 | Yavitz | |
| 6,062,215 A | 5/2000 | Leininger et al. | |
| 6,098,628 A | 8/2000 | Funk | |
| 6,142,982 A | 11/2000 | Hunt et al. | |
| 6,222,090 B1 | 4/2001 | Weston | |
| 6,328,709 B1 | 12/2001 | Hung et al. | |
| 6,458,109 B1 | 10/2002 | Henley et al. | |
| 6,484,716 B1 | 11/2002 | Leininger et al. | |
| D469,175 S | 1/2003 | Hall et al. | |
| 6,553,998 B2 * | 4/2003 | Heaton | A61F 13/023 128/897 |
| D475,134 S | 5/2003 | Randolph | |
| 6,695,823 B1 | 2/2004 | Lina et al. | |
| D488,588 S | 4/2004 | Murphy | |
| 6,764,462 B2 | 7/2004 | Risk et al. | |
| 6,767,334 B1 | 7/2004 | Randolph | |
| 6,767,344 B2 | 7/2004 | Suzuki | |
| 6,814,079 B2 | 11/2004 | Heaton et al. | |
| 6,824,533 B2 | 11/2004 | Risk, Jr. et al. | |
| 6,856,821 B2 | 2/2005 | Johnson | |
| 6,936,037 B2 | 8/2005 | Bubb et al. | |
| 6,951,553 B2 | 10/2005 | Bubb et al. | |
| 7,108,683 B2 | 9/2006 | Zamierowski | |
| 7,154,017 B2 * | 12/2006 | Sigurjonsson | A61F 13/0203 602/41 |
| 7,532,953 B2 | 5/2009 | Vogel | |
| 7,534,240 B1 | 5/2009 | Johnson | |
| 7,608,066 B2 | 10/2009 | Vogel | |
| 7,790,945 B1 | 9/2010 | Watson, Jr. | |
| 7,837,673 B2 | 11/2010 | Vogel | |
| 7,909,805 B2 | 3/2011 | Weston | |
| 7,964,766 B2 | 6/2011 | Blott et al. | |
| D642,594 S | 8/2011 | Mattson et al. | |
| D648,353 S | 11/2011 | Mattson et al. | |
| 8,080,702 B2 | 12/2011 | Blott et al. | |
| 8,142,405 B2 | 3/2012 | Vogel | |
| 8,187,237 B2 | 5/2012 | Seegert | |
| 8,529,532 B2 | 9/2013 | Pinto et al. | |
| 8,563,604 B2 | 10/2013 | Palefsky et al. | |
| 8,708,982 B2 | 4/2014 | Lin | |
| 8,821,419 B1 | 9/2014 | Beek | |
| 9,782,512 B2 * | 10/2017 | Blucher | A61F 13/00063 |
| 9,913,757 B2 | 3/2018 | Vitaris | |
| 9,925,361 B2 | 3/2018 | Lin | |
| 2001/0029956 A1 | 10/2001 | Argenta et al. | |
| 2001/0041188 A1 | 11/2001 | Gibbins et al. | |
| 2002/0017304 A1 | 2/2002 | Heaton et al. | |
| 2002/0143286 A1 | 10/2002 | Tumey | |
| 2002/0155164 A1 | 10/2002 | Figley et al. | |
| 2003/0014022 A1 | 1/2003 | Lockwood et al. | |
| 2003/0021775 A1 | 1/2003 | Freeman | |
| 2003/0040687 A1 | 2/2003 | Boynton et al. | |
| 2003/0050594 A1 | 3/2003 | Zamierowski | |
| 2003/0212357 A1 | 11/2003 | Pace | |
| 2003/0219469 A1 | 11/2003 | Johnson et al. | |
| 2004/0006319 A1 | 1/2004 | Lina et al. | |
| 2004/0010207 A1 | 1/2004 | Flaherty et al. | |
| 2004/0073151 A1 | 4/2004 | Weston | |
| 2004/0093026 A1 | 5/2004 | Weidenhagen et al. | |
| 2004/0126413 A1 * | 7/2004 | Sigurjonsson | A61F 13/0203 424/445 |
| 2004/0153032 A1 | 8/2004 | Garribotto et al. | |
| 2004/0170703 A1 | 9/2004 | Hoekstra et al. | |
| 2005/0137521 A1 | 6/2005 | Stenzler | |
| 2005/0220849 A1 | 10/2005 | Hickey | |
| 2005/0228340 A1 | 10/2005 | Cleary et al. | |
| 2006/0127462 A1 | 6/2006 | Canada et al. | |
| 2006/0146234 A1 | 7/2006 | Bear et al. | |
| 2006/0185670 A1 | 8/2006 | Loori et al. | |
| 2007/0041960 A1 | 2/2007 | Freeman et al. | |
| 2007/0118096 A1 | 5/2007 | Smith et al. | |
| 2008/0140029 A1 | 6/2008 | Smith et al. | |
| 2009/0258058 A1 * | 10/2009 | Thomas | A61K 9/7015 514/1.1 |
| 2009/0312723 A1 | 12/2009 | Blott et al. | |
| 2010/0268128 A1 | 10/2010 | Randolph | |
| 2010/0298792 A1 | 11/2010 | Weston et al. | |
| 2011/0160686 A1 | 6/2011 | Ueda et al. | |
| 2012/0029449 A1 | 2/2012 | Khosrowshahi | |
| 2013/0053795 A1 | 2/2013 | Coulthard et al. | |
| 2013/0053806 A1 * | 2/2013 | Guillo | A61L 15/26 604/369 |
| 2013/0165837 A1 * | 6/2013 | Addison | A61L 15/26 602/44 |
| 2013/0211318 A1 | 8/2013 | Croizat et al. | |
| 2013/0231623 A1 | 9/2013 | Richard | |
| 2013/0303975 A1 | 11/2013 | Gvodas, Jr. | |
| 2014/0081192 A1 * | 3/2014 | Wenske | A61F 13/00 602/44 |
| 2014/0114268 A1 * | 4/2014 | Auguste | A61F 13/02 604/368 |
| 2014/0155790 A1 | 6/2014 | Argenta et al. | |
| 2014/0207027 A1 | 7/2014 | Navia et al. | |
| 2014/0309574 A1 * | 10/2014 | Cotton | A61F 13/00021 602/44 |
| 2015/0005678 A1 | 1/2015 | Wall | |
| 2015/0088085 A1 * | 3/2015 | Rovaniemi | A61F 13/0206 604/385.03 |
| 2015/0119832 A1 * | 4/2015 | Locke | A61F 13/00063 604/319 |

(56) References Cited

U.S. PATENT DOCUMENTS

| | | | |
|---|---|---|---|
| 2016/0000610 A1* | 1/2016 | Riesinger | A61F 13/00063 604/369 |
| 2016/0074232 A1 | 3/2016 | Vitaris et al. | |
| 2016/0128894 A1 | 5/2016 | Horton et al. | |
| 2016/0166781 A1 | 6/2016 | Sarangapani et al. | |
| 2016/0256665 A1* | 9/2016 | Doshi | F16M 13/022 |
| 2016/0262944 A1* | 9/2016 | Shmuelovitch | A61F 13/00046 |
| 2017/0119940 A1 | 5/2017 | Quisenberry | |
| 2018/0169395 A1 | 6/2018 | Lin | |
| 2019/0029886 A1 | 1/2019 | Lin | |
| 2019/0030223 A1 | 1/2019 | Lin | |
| 2019/0030224 A1 | 1/2019 | Lin | |
| 2019/0030225 A1 | 1/2019 | Lin | |
| 2019/0030226 A1 | 1/2019 | Lin | |

FOREIGN PATENT DOCUMENTS

| | | |
|---|---|---|
| CN | 101969902 B | 2/2013 |
| CN | 102985096 A | 3/2013 |
| CN | 104024498 A | 9/2014 |
| CN | 106659590 A | 5/2017 |
| EP | 0206646 | 12/1986 |
| EP | 0940131 A2 | 9/1999 |
| EP | 1219311 | 7/2004 |
| EP | 1018967 | 8/2004 |
| EP | 1674898 | 6/2006 |
| EP | 1901686 | 7/2014 |
| EP | 2995324 A1 | 3/2016 |
| EP | 3156016 | 4/2017 |
| GB | 288220 | 8/1928 |
| GB | 2265314 | 9/1993 |
| GB | 2329127 | 3/1999 |
| GB | 2351025 | 12/2000 |
| GB | 2365350 | 2/2002 |
| GB | 3157484 B1 * | 6/2015 |
| GB | 2496310 B | 10/2015 |
| WO | 9605873 | 2/1996 |
| WO | 0059418 | 10/2000 |
| WO | 0059424 | 10/2000 |
| WO | 03049660 | 6/2003 |
| WO | 2003092620 | 11/2003 |
| WO | 2004060148 | 7/2004 |
| WO | 2005009488 | 2/2005 |
| WO | 2005046761 A1 | 5/2005 |
| WO | 2006081403 A1 | 8/2006 |
| WO | 2009141820 A1 | 11/2009 |
| WO | 2011130246 A2 | 10/2011 |
| WO | 2013066694 A2 | 5/2013 |
| WO | 2013123005 A1 | 8/2013 |
| WO | 2015193257 A1 | 12/2015 |
| WO | 2019027806 A1 | 2/2019 |
| WO | 2019027807 A1 | 2/2019 |
| WO | 2019027808 A1 | 2/2019 |
| WO | 2019027809 A1 | 2/2019 |
| WO | 2019027810 A1 | 2/2019 |

OTHER PUBLICATIONS

International Search Report for International Application No. PCT/US2018/043955 dated Oct. 17, 2018.
International Search Report for International Application No. PCT/US2018/043957 dated Oct. 19, 2018.
International Search Report for International Application No. PCT/US2018/043959 dated Oct. 15, 2018.
International Search Report for International Application No. PCT/US2018/043962 dated Oct. 16, 2018.
Cardinal Health NPWT Pro Family, Cardinal Health, Waukegan, IL, 2015.
Cardinal Health SVED Clinician User Manual, Cardinal Health, Waukegan, IL, 2015.
Cardinal Health SVED Wound Care Anywhere, Cardinal Health, Waukegan, IL, 2015.
Cardinal Health SVED Patient User Manual, Cardinal Health, Waukegan, IL, 2015.
ITI Brings Hospitals New Value Model For Wound Care, Innovative Therapies, Inc. Copyright 2013 PR Newswire.
Office Action From Taiwan Republic of China Patent Office.
Application Guide: Pico multisite with softport technology applied to the heel, PCPE-48-0717-UE, Smith & Nephew, Inc. 2017.
Avance® Clinician's Guidelines, Revision Feb. 2017, Mölnlycke Health Care US, LLC, Norcross, GA 30092.
Borgquist, O., R. Ingemansson, M Malmsjö, Effects of negative pressure wound therapy on regional blood flow, wound contraction and fluid removal—Examining low pressure levels, intermittent and variable therapy, 24th Annual Clinical Symposium on Advances in Skin & Wound Care, San Antonio, Texas, USA—Oct. 22-25, 2009.
Borgquist, Ola, et al. Wound Edge Microvascular Blood Flow during Negative-Pressure Woulnd Therapy: Examining the Effects of Pressures from −10 to −175 mmHg, PRSJournal, vol. 125, No. 2, 2010, 502-509.
Chanden K. Sen, Wound healing essentials: Let there be oxygen, Wound Rep Reg (2009) 17 1-18.
Eriksson, et al., Wet wound healing: from laboratory to patients to gene therapy, The American Journal of Surgery 188 (Suppl to Jul. 2004) 36S-41S.
EZCare Negative Pressure Wound Therapy, V1STA Negative Pressure Wound Therapy, Negative Pressure Wound Therapy Clinical Guidelines, BS-0039-0808, Smith & Nephew.
Final Rejection, U.S. Appl. No. 15/663,710, dated Nov. 25, 2019.
Ghatak, Schlanger, Ganesh, Lambert, Gordillo, Martinsek and Roy, A Wireless Electroceutical Dressing Lowers Cost of Negative Pressure Wound Therapy, Adv Wound Care (New Rochelle) 4(5): 302-311, May 2015.
Mialsmjo, Md, et al., Negative pressure wound therapy using gauze or polyurethane open cell foam: similar effects on would edge microvascular blood flow, Lund University, 1 page.
Miederauer, Mark Q. et al. Continuous diffusion of oxygen improves diabetic foot ulcer healing when compared with a placebo control: a randomised, double-blind, multicentre study, J. Wound Care, N. American Supplement, vol. 27, No. 9, Sep. 2018.
Non Final Rejection, U.S. Appl. No. 15/663,710, dated Jul. 11, 2019.
Non-Final Office Action, U.S. Appl. No. 15/663,708, dated Nov. 7, 2019.
Non-Final Rejection, U.S. Appl. No. 15/663,709, dated Oct. 10, 2019.
Non-Final Rejection, U.S. Appl. No. 15/663,713, dated Jun. 28, 2019.
Notice of References Cited, U.S. Appl. No. 15/663,708.
Notice of References Cited, U.S. Appl. No. 15/663,709.
Notice of References Cited, U.S. Appl. No. 15/663,710.
Notice of References Cited, U.S. Appl. No. 15/663,713.
Prevena Incision Management System, Clinician Guide, 390061 Rev C, KCI Licensing Inc., 2009.
Prevena Incision Management System, Product Monograph, KCI Licensing Inc., 2010.
Prospera Negaitve Pressure Wound Therapy, Pro-I, Advancing the Art and Science of NPWT, Prospera, Ft. Worth, Tx, 2008. MR-125-04/08.
RENASYS Negative Pressure Wound Therapy, Pico Single Use Negative Pressure Wound Therapy System, NPCE-48-0613-NAE, Smith & Nephew, Inc., 2013.
V.A C. Ulta Quick Reference Guide, KCI Licensing Inc., 2013.
V.A.C. Ulta™ Negative Pressure Wound Therapy System, KCI Licensing Inc., Apr. 17, 2016.
Cardinal Health SVED, "Clinitial Quick Reference Guide", Cardinal Health, the Netherlands, 2015, 2 pages.

* cited by examiner

WOUND THERAPY APPARATUS WITH SCAR MODULATION PROPERTIES AND RELATED METHODS

CROSS-REFERENCE TO RELATED APPLICATIONS

This application hereby incorporates by reference in the entirety herein the co-pending U.S. patent application Ser. No. 15/663,708 entitled "DEFORMATION RESISTANT WOUND THERAPY APPARATUS AND RELATED METHODS OF USE," co-pending U.S. patent application Ser. No. 15/663,709 entitled "AUGMENTED PRESSURE THERAPY FOR WOUNDS," co-pending U.S. patent application Ser. No. 15/663,710 entitled "CONTROL APPARATUS AND RELATED METHODS FOR WOUND THERAPY DELIVERY," co-pending U.S. patent application Ser. No. 15/663,713 entitled "WOUND COVER APPARATUS AND RELATED METHODS OF USE," all by Edward D. Lin as inventor and applicant and filed on 29 Jul. 2017.

BACKGROUND OF THE INVENTION

Field

This invention relates to medical devices, and more particularly, to wound therapy apparatus and related compositions of matter and methods of use.

Related Art

Wounds afflict hundreds of millions of people globally. Wounds are often traumatic, although the number of incisional wounds number over 71 million in the US. Many wounds heal with a scar that may be prominent, and, thus, stigmatize, affect esthetics, and diminish self-esteem. Hypertrophic scars such as keloids may limit function due to the thickness and restrictive nature of the scar tissue.

In order for an incisional wound to heal well and quickly with no visible or minimally visible scar formation, multiple important factors must be present, including adequate blood flow and oxygenation, absence of infection, proper moisture balance, even apposition (alignment) of wound edges with a homogenous dispersion of tension across the entire wound area. The classic ugly "railroad track" scar is typically caused by focal tension exerted by suture lines, which can be worsened yet further by a certain degree of wound dehiscence (wound edge separation). Silicone in the form of a sheet has been applied to the scar of a completely- or long-healed wound including keloids to induce collagen reconfiguration with the therapeutic goal of a less prominent scar. The silicone sheet is a barrier to exudate transfer, and, therefore, by conventional wisdom, is not suitable for use during actual wound healing.

Similarly, while various dressing including bandages, covers, compresses, and so forth that are applied to wounds during healing are labeled as including silicone, the "silicone" label refers to the presence of a silicone (instead of, for example, an acrylic) adhesive that anchors the dressing to the skin surface. The silicone in these dressings, is not in direct contact with the wound, and because the silicone adhesive is easy to peel off the skin. These dressings take weeks or longer to work, and may be ineffective in mitigating scarring.

Accordingly, there is a need for improved apparatus as well as related methods for wound therapy that may, for example, reduce scarring while protecting the wound during the healing process.

BRIEF SUMMARY OF THE INVENTION

These and other needs and disadvantages may be overcome by the wound therapy apparatus and related methods of use disclosed herein. Additional improvements and advantages may be recognized by those of ordinary skill in the art upon study of the present disclosure.

In various aspects, the wound therapy apparatus disclosed herein may include a distal layer to contact a wound bed, the distal layer comprised of silicone, and fenestrations disposed about the distal layer pass between a distal side of the distal layer and a proximal side of the distal layer to communicate between the distal side and the proximal side. A pad may cooperate with the proximal side of the distal layer to receive exudate communicated through the distal layer from the wound bed via the fenestrations, in various aspects. Various materials including medicament(s) may be communicated to the wound bed through the distal layer via the fenestrations, in various aspects. A structural member may be included in various aspects to secure the distal layer and pad to a skin surface, in various aspects.

Methods of use of the wound therapy apparatus are disclosed herein. In various aspects, the methods of use may include the step of contacting a distal side of a distal layer of said wound therapy apparatus with a wound bed, the distal layer comprising silicone with fenestrations passing between the distal side of the distal layer and a proximal side of the distal layer. The methods of use may include the step of removing exudate from the wound bed by communicating exudate from the distal side of the distal layer to the proximal side of the distal layer. The methods of use may include the step of moderating scar formation by contacting the wound bed with the distal layer comprising silicone throughout healing of the wound bed.

This summary is presented to provide a basic understanding of some aspects of the apparatus and methods disclosed herein as a prelude to the detailed description that follows below. Accordingly, this summary is not intended to identify key elements of the apparatus, methods, and compositions of matter disclosed herein or to delineate the scope thereof.

Figure 1A:
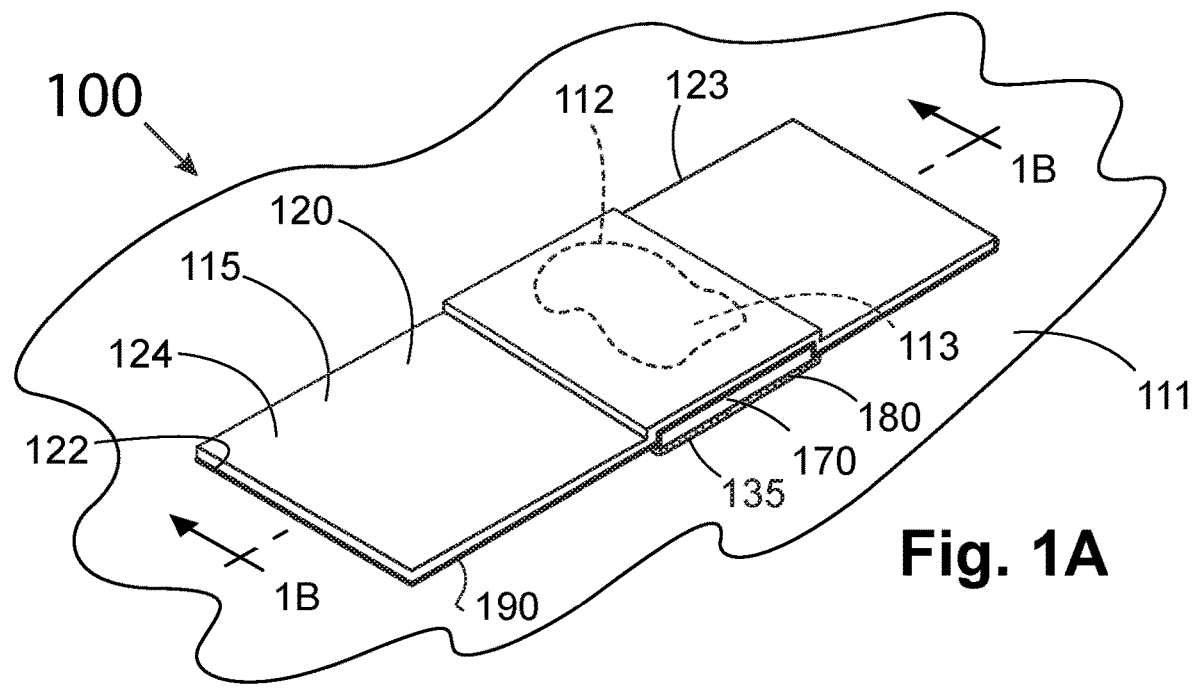
FIG. 1A illustrates by perspective view an exemplary implementation of a wound therapy apparatus.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A wound therapy apparatus is disclosed herein. In various aspects, the wound therapy apparatus includes a distal layer that contacts a wound bed, the distal layer being comprised, at least in part, of silicone that may be generally in the form of a sheet. The wound bed may be in various states of healing ranging from a newly created wound bed to a wound bed that has nearly healed over. The distal layer includes fenestration that pass between a distal side of the distal layer that may contact the wound bed and a proximal side of the distal layer, in various aspects. A pad may cooperate with the fenestrations on the proximal side of the distal layer to absorb exudate communicated from the wound bed through the fenestrations or to communicate material(s) to the wound bed through the fenestrations, in various aspects.

In some aspects, the wound therapy apparatus includes a structural member that cooperates mechanically with the distal layer and with the pad, if present, and the structural member may be adhesively attachable to a skin surface around the wound bed to hold the distal layer in contact with the wound bed by an adhesive layer disposed about the structural member. The structural member may protect the wound bed, the distal layer, and the pad, when the pad is present. The structural member may maintain the distal layer and the pad in relation to one another, in certain aspects.

Methods of use of the wound therapy apparatus are disclosed herein. In various aspects, the methods of use may include the step of contacting the distal side of the distal layer with an unhealed wound bed, the distal layer comprising silicone with fenestrations passing between the distal side of the distal layer and a proximal side of the distal layer, and the step of removing exudate from the wound bed by communicating exudate from the distal side of the distal layer to the proximal side of the distal layer. Methods of use of the wound therapy apparatus may include the step of moderating scar formation by exposing the wound bed to the distal layer comprising silicone, at least in part, and having fenestrations therethrough throughout healing of the wound bed. Methods of use of the wound therapy apparatus may include the step of intermittently replacing a wound interface throughout healing of the wound bed, the wound interface, in certain aspects, comprising the distal layer, the pad, and the structural member. Methods of use of the wound therapy apparatus may include the step of intermittently replacing the distal layer during healing of the wound bed.

Silicone, as used herein, includes siloxane, various polysiloxanes, silicone-like materials, and various combinations thereof that may be generally solid. Silicone may have the chemical formula $[R_2SiO]_n$, where R is an organic group. Silicone may include, for example, silicone polymers having an average molecular weight in excess of 100,000 (e.g., between about 100,000 and about 10,000,000). Examples may include, but are not limited to, crosslinked siloxanes (e.g., crosslinked dimethicone or dimethicone derivatives), copolymers such as stearyl methyl-dimethyl siloxane copolymer, polysilicone-11 (a crosslinked silicone rubber formed by the reaction of vinyl terminated silicone and (methylhydro dimethyl)polysiloxane in the presence of cyclomethicone), cetearyl dimethicone/vinyl dimethicone crosspolymer (a copolymer of cetearyl dimethicone crosslinked with vinyl dimethyl polysiloxane), dimethicone/phenyl vinyl dimethicone crosspolymer (a copolymer of dimethylpolysiloxane crosslinked with phenyl vinyl dimethylsiloxane), and dimethicone/vinyl dimethicone crosspolymer (a copolymer of dimethylpolysiloxane crosslinked with vinyl dimethylsiloxane).

Fluid, as used herein, includes, liquid(s), gas(ses), and combinations thereof. In various aspects, material, as used herein, includes solid(s), liquid(s), and gas(ses), and material may include one or more medicament(s). Exudate, as used herein, includes, for example, proteinaceous liquids exuded from the wound bed, along with various plasma, blood and cellular components, and other liquids that may be exuded by the wound bed. Exudate may also include other liquids such as perspiration from the skin surface surrounding the wound bed, other liquids as may be present on or about the wound bed or the skin surface proximate the wound bed. Exudate, as used herein, may include gas(ses) such as $CO_2$ and water vapor exhaled from the skin surface.

In various aspects, the term fluid-tight or related terms, as used herein, means sufficiently leak-resistant to allow insufflation or vacuum suction to create pressure $p_0$ that may be above or below ambient pressure $p_{amb}$. The term fluid-tight means sufficiently leak-resistant to substantially retain fluids including both gasses and liquids within the enclosed space, in certain aspects. In certain aspects, fluid tight means sufficiently leak-resistant to maintain pressure $p_0$ within the enclosed space that may be above or below ambient pressure $p_{amb}$.

Wound bed, as used herein, means a focal breach in the external surface of normal skin, for example, from trauma (such as abrasion, avulsion, tearing, piercing, cutting, chemical or thermal injury) or microbial infection. The wound bed may include varying degrees of exposure of underlying layers and structures, along with possible infections and tissue changes. The wound bed represents an unhealed wound. In contrast, a healed wound is a skin surface that was previously injured but the focal breach is now entirely sealed and covered by varying amounts of epidermis and scar tissue.

As used herein the terms distal and proximal are relative, not necessarily absolute positional terms defined from the point of view of a caregiver, including physicians, nurses and technicians, treating a patient with the wound therapy apparatus. A distal portion of the wound therapy apparatus may be oriented toward the patient while a proximal portion of the wound therapy apparatus may be oriented toward the physician. When deployed, for example, a distal portion of the wound therapy apparatus may be closer to the patient while a proximal portion of the wound therapy apparatus may be closer to the caregiver. As a further example, a distal surface in a multi-layer wound interface is closer to the wound bed, but not necessarily the layer in contact with or closest to the wound bed.

Figure 1B:
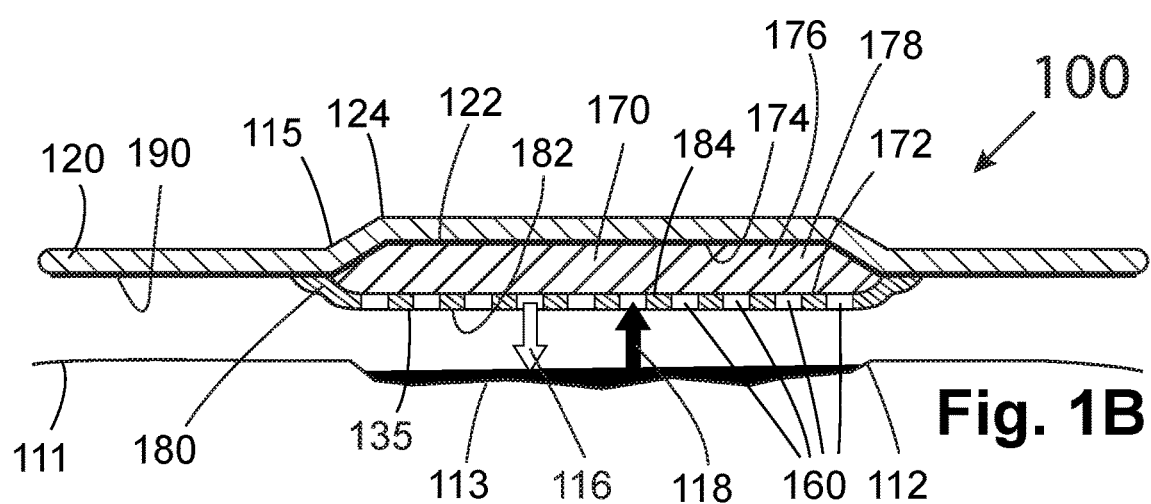
FIG. 1B illustrates by cross-sectional view through section 1A-1A of the exemplary implementation of the wound therapy apparatus of FIG. 1A.
Figure 1C:
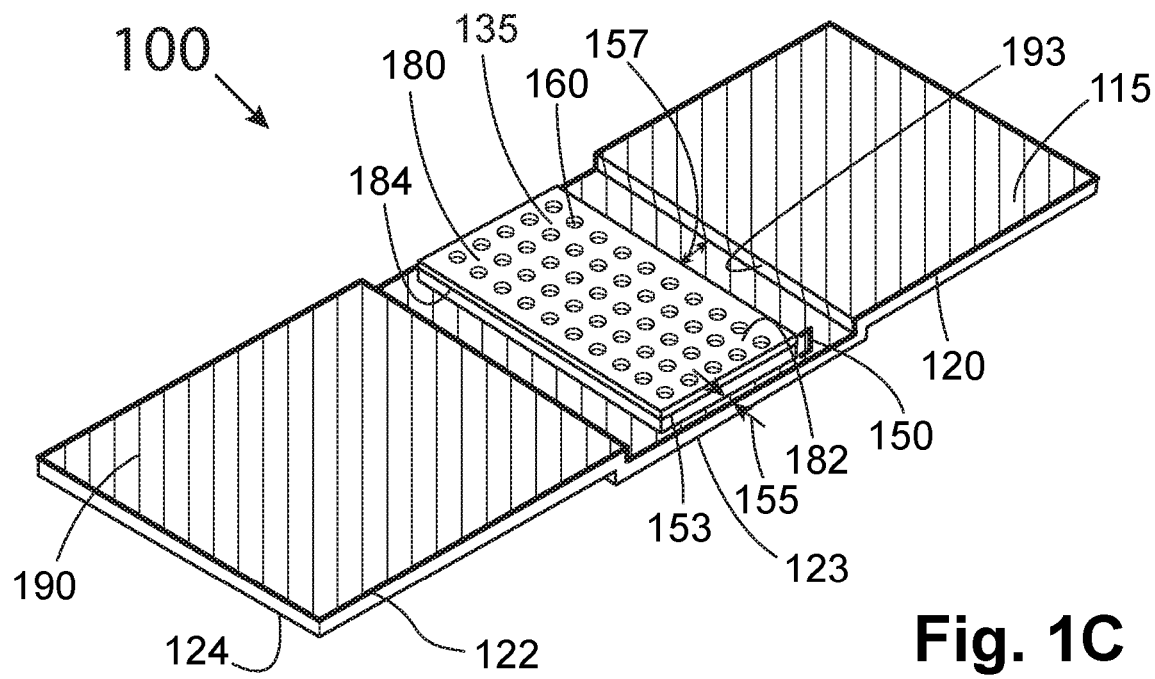
FIG. 1C illustrates by another perspective view the exemplary implementation of the wound therapy apparatus of FIG. 1A.

FIGS. 1A, 1B, 1C illustrates exemplary wound therapy apparatus 100. As illustrated in FIGS. 1A and 1B, wound therapy apparatus 100 includes wound interface 115 secured to skin surface 111 to cover wound bed 113. Wound interface 115 includes structural member 120, pad 170, distal layer 180, and adhesive 190, as illustrated, and wound interface 115 is secured to skin surface 111 by adhesive 190.

FIG. 1B depicts cross-section 1B-1B of FIG. 1A with wound interface 115 illustrated as set apart from wound bed 113 and skin surface 111 for purposes of clarity of explanation, it should be understood that wound interface 115 is actually secured to skin surface 111. In this implementation, distal side 182 of distal layer 180 contacts wound bed 113 and adhesive 190 contacts skin surface 111 outside of wound boundary 112 of wound bed 113 so that there is no contact between adhesive 190 and wound bed 113 when wound interface is secured to skin surface 111.

As illustrated in FIG. 1B, pad 170 is interposed between structural member 120 and distal layer 180, distal side 172 of pad 170 is in biased engagement with proximal side 184 of distal layer 180, and proximal side 174 of pad 170 is faced toward distal side 122 of structural member 120. Pad 170 in biased engagement with distal layer 180 forms a combination structure 150, as illustrated in FIG. 1C. In some implementations, proximal side 174 of pad 170 may be secured to distal side 122 of structural member 120, while, in other implementations, proximal side 174 of pad 170 may be generally disposed about distal side 122 of structural member 120 but engaged with structural member 120 by engagement with distal layer 180 and not directly engaged with structural member 120. In this implementation, structural member 120, pad 170, and distal layer 180 are engaged with respect to one another in various ways, and structure 150 is secured to structural member 120 in various ways, as would be readily recognized by those of ordinary skill in the art upon study of this disclosure.

Structural member 120 may be, formed, for example, of a layer of polyurethane, fabric, polyethylene, polyvinyl chloride, or latex, and structural member 120 may be conformable to skin surface 111 proximate wound bed 113. In some implementations, structural member 120 and adhesive 190 have a suitable moisture-vapor transfer rate (MVTR) that allows for passage of $O_2$, $CO_2$, and water vapor from distal side 122 to proximal side 124 so that the skin surface 111 underneath may breathe, while generally excluding unwanted elements such as bacteria or water to protect wound bed 113 from external contamination. Although "breathable" in terms of transpiration, structural member 120 and adhesive 190 may be fluid tight as defined herein such that wound interface 115 is occlusive and usable for pressure therapy. Adhesive 190 may be formed, for example, of silicone based adhesive, acrylic, hydrocolloid, or other suitable medical adhesives. Adhesive 190 as a silicone based adhesive may have a lower tack than acrylic adhesive, and thus may be used when skin surface 111 is delicate or sensitive such as in neonates and the elderly to avoid damage to the skin surface 111 during removal of wound interface 115.

Because distal layer 180 is formed, at least in part, of silicone 135, in this implementation, distal layer 180 may not adhere to wound bed 113, for example, by adhesion of granulation tissues in wound bed 113 to distal side 182 of distal layer 180. In addition to such non-adhesion properties, the silicone 135 of distal layer 180 may modulate the expression of two counteracting growth factors, fibroblast growth factor β (FGF β) and tumor growth factor β (TGF β) in wound bed 113. TGF β may stimulate fibroblasts to synthesize collagen and fibronectin. FGF β may normalize the collagen synthesis in wound bed 113 and may increases the level of collagenases that break down excess collagen. Distal layer 180 may thus restore the homeostatic balance of fibrogenesis and fibrolysis in wound bed 113. Distal layer 180 may increase hydration of stratum corneum, thereby facilitating regulation of fibroblast production and reduction in collagen production in wound bed 113. Such reversal of excessive collagen formation may result in a softer and flatter scar as wound bed 113 heals. The silicone 135 of distal layer 180 may reduce itching and discomfort associated with wound bed 113 as wound bed 113 heals.

Because silicone 135 has a high coefficient of friction, when wound bed 113 is formed as a linear wound, including an incisional wound that is at risk of dehiscence, distal layer 180 may aid in apposing the two sides of the linear wound together, thereby reducing the likelihood of healing by secondary intentions that would, in turn, result in a prominent wide scar. Distal layer 180 may provide additional benefits to wound bed 113 when contacted with wound bed 113, in various other implementations. Texture, such as texture 864 (see FIG. 8), included on distal side 182 of distal layer 180 may increase the coefficient of friction of distal side 182 of distal layer 180.

As illustrated in FIG. 1B, distal layer 180 includes fenestrations 160 that extend between distal side 182 and proximal side 184 of distal layer 180 for communication between distal side 182 and proximal side 184 of distal layer 180. For example, exudate 118 exuded by wound bed 113 may be communicated from distal side 182 of distal layer 180 to proximal side 184 of distal layer 180 through fenestrations 160, for example, drawn by capillary action towards pad 170. Pad 170 then absorbs exudate 118 communicated from wound bed 113 through distal layer 180 via fenestrations 160. Accordingly, pad 170 prevents buildup of exudate 118 in wound bed 113 or on skin surface 111 and resultant maceration from prolonged contact with exudate 118. Material 116 such as air, oxygen, and medicament 176 may be communicated from pad 170 through fenestrations 160 from proximal side 184 to distal side 182 of distal layer 180 to wound bed 113, as illustrated in FIG. 1B. Material 116 may be communicated to wound bed 113 through fenestrations 160 by various transport mechanisms such as fluid flow, capillary action, and diffusion.

Fenestrations 160 may be sized in both quantity, distribution about distal layer, and aperture size to optimize transfer of exudate 118 from wound bed 113, for example, during different stages of healing of wound bed 113. For example, when wound bed 113 is formed as an acute wound, exudate 118 from wound bed 113 may be thin (less viscous), and, thus, the fenestrations 160 may be relatively small. As another example, when wound bed 113 is formed as a chronic wound, exudate 118 from wound bed 113 may be more viscous, and, accordingly, fenestrations 160 may be larger or more plentiful.

Pad 170 may be formed, at least in part of, for example, polyvinyl alcohol, polyurethane foam, polyurethane foam with polyethylene glycol (PEG) that may enhance absorption and transport characteristics, gauze, fiber-like materials such as sodium carboxymethyl cellulose hydrofiber (Aquacel) or knitted synthetic fibers such as polypropylene and polyamide or a combination of both with hydrophobic polypropylene fiber predominant proximate distal side 172 and hydrophilic polyamide fibers predominant proximate proximal side 174 to conduct exudate 118 away from wound bed 113. An elastomeric fiber such as a polyester-polyurea (e.g., Spandex or Lycra) may additionally be incorporated in pad 170 to lend stretchability and conformability to pad 170.

Pad 170 may include various material(s) 116 including medicament(s) 176, such as, for example, antibiotics, analgesics such as local anesthetics, COX-2 inhibitors and nonsteroidal anti-inflammatory drugs, angiotensin-converting enzyme inhibitors, anti-microbial chitosan or silver compounds, bioactive factors such as the TGF-β superfamily; collagen synthesis inhibitors; cytokines, various formulations of placenta, including placental matrix powder, etc., for delivery to wound bed 113 through distal layer 180 via fenestrations 160. Pad 170 may include various indicator(s) 178 such as, for example, a florescent dye that indicates the pH under UV light thus indicating the health of the wound bed 113, and structural member may be formed, at least in part, of transparent or translucent material to allow viewing of the indicator. The materials that form pad 170 may be adjusted to accommodate such indicators or the delivery of medicament(s) 176 to the wound bed 113. Pad 170 may, for example, include multiple layers formed of differing materials or each of the multiple layers including various combinations of medicament(s) 176 or indicator(s) 178.

In certain implementations, medicament 178 as a liquid formulation may be pre-manufactured as a containment device adjacent to or connected to layer 170 and released by puncturing, removing, or opening a partition in the containment device prior to applying wound interface 115 to wound bed 113. Alternatively, such separate containment devices may be added to or engaged with layer 170 prior to application of wound interface 115 via a syringe or via optional injection or intake ports.

As illustrated in FIG. 1C, perimeter 153 of structure 150 is offset from edge 123 of structural member 120 by length 155 to prevent exposure of structure 150 when structural member 120 is secured to skin surface 111. In other implementations, length 155 may be negligible so that perimeter 153 is coextensive with edge 123. Perimeter 153 of structure 150 may be offset from adhesive 190 by length 157. Length 157 may be selected to avoid contact between wound bed 113 and adhesive 190 when wound interface 115 is secured to skin surface 111 and distal layer 180 contacts wound bed 113.

As illustrated in FIG. 1C, distal layer 180 and pad 170 of wound therapy apparatus 100 are coextensive with one another in structure 150, but this need not be the case in other implementations. Structural member 120 is illustrated as largely rectangular in shape with structure 150 disposed medially, and structure 150 is illustrated as having a rectangular shape. Structure 150 may be variously disposed about structural member 120, and structure 150 and structural member 120 may have various other geometric shapes, such as square, circular, oval, and the shapes of structural member 120 and structure 150 may be similar to one another or dissimilar from one another, in other implementations. Such other geometric shapes and dispositions may have equivalencies of lengths, such as lengths 155, 157, between a structure, such as structure 150, and an edge, such as edge 123, 193, as may be appropriate. For clarity of explanation, FIG. 1C, as well as the other Figures illustrative of wound therapy apparatus 100, does not show release liner layer(s) that may be included in various implementations of wound therapy apparatus 100, as would be readily recognized by those of ordinary skill in the art upon study of this disclosure.

Figure 2:
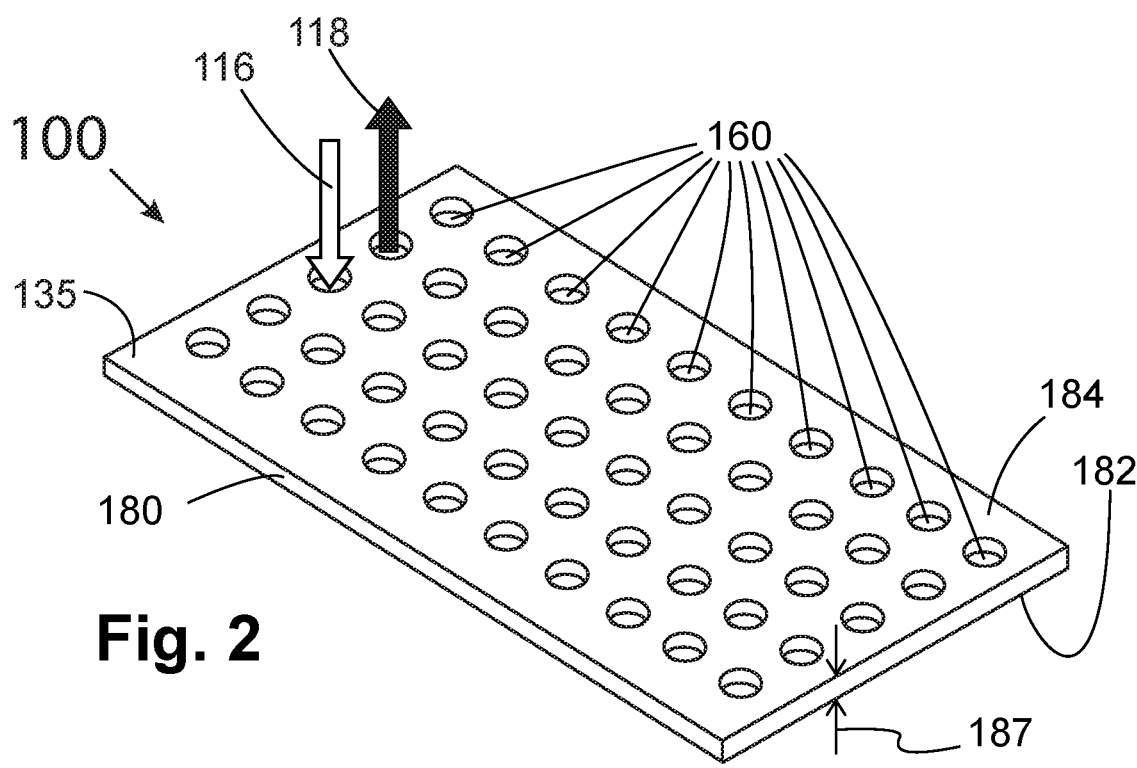
FIG. 2 illustrates by perspective view portions of the exemplary implementation of the wound therapy apparatus of FIG. 1A.

FIG. 2 illustrates distal layer 180 of exemplary wound therapy apparatus 100 including fenestrations 160 disposed about distal layer 180 that pass through distal layer 180 between distal side 182 and proximal side 184. Exudate 118 may be communicated between distal side 182 and proximal side 184 of distal layer 180 through the fenestrations 160 and material 116 may be communicated between proximal side 184 and distal side 182 of distal layer 180 through fenestrations 160. Fenestrations 160 in exemplary wound therapy apparatus 100 are illustrated as circular in geometry defining cylinders between proximal side 184 and distal side 182. Fenestrations, such as fenestrations 160, may have different shapes and sizes and may be distributed in regular and irregular patterns, in various implementations.

Thickness 187 of distal layer 180 may vary depending upon the type of wound bed 113 and degree of exudation with which wound interface 115 is employed. Thickness 187 may range from about 0.1 mm to about 2 mm, in certain implementations. Thickness 187 may range from about 0.2 mm to about 1 mm, in certain implementations. Distal side 182 may be flat or may include various textures, such as texture 864, as may depend upon the type of wound bed 113 with which wound interface 115 is employed. As thickness 187 increases, distal layer 180 may become less susceptible to stretch and distortion. In various implementations, the size of fenestrations 160 in distal layer 180 may generally range from about 250 microns to 2500 microns in diameter or equivalent, or from about 500 microns (#35 Mesh) to about 1000 microns (#18 Mesh) in diameter or equivalent. The number of fenestrations 160 in distal layer 180 per $cm^2$ may range from about 25 per $cm^2$ to about 200 per $cm^2$, in certain implementations.

Figure 3:
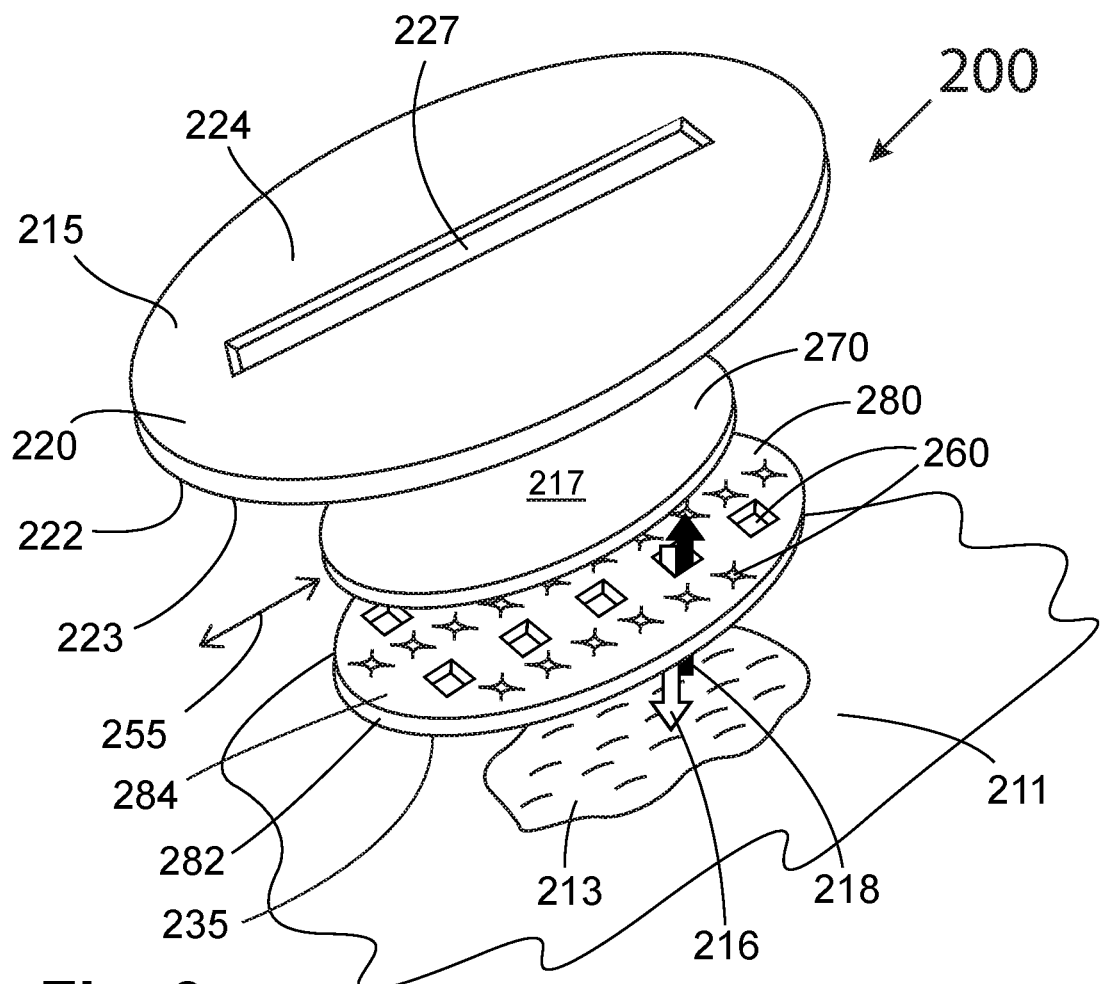
FIG. 3 illustrates by perspective view a second exemplary implementation of a wound therapy apparatus in exploded relation with a wound bed and skin surface.

As illustrated in FIG. 3, wound therapy apparatus 200 includes wound interface 215, and wound interface includes structural member 220, pad 270, and distal layer 280. Structural member 220, pad 270, and distal layer 280 are oblong in shape, and pad 270 is disposed between distal layer 280 and structural member 220, as illustrated. Border 223 of length 255 extends perimetrically around distal side 222 of structural member 220 to surround pad 270 in combination with distal layer 280. Adhesive, such as adhesive 190, 690, 790, disposed on at least portions of border 223 may secure wound interface 215 to skin surface 211 around wound bed 213. In some implementations of wound interface 215, structural member 220 is fluid tight and the adhesive sealingly secures wound interface 215 to the skin surface 211 around wound bed 213 to enclose pad 270 and distal layer 280, thereby forming an enclosed space 217 that is fluid tight over wound bed 213, i.e., wound interface 215 secured to skin surface 211 is occlusive. In such implementations, a port may be disposed about wound interface 215 for fluid communication through structural member 220 with enclosed space 217.

As illustrated in FIG. 3, fenestrations 260 pass between distal side 282 and proximal side 284 of distal layer 280. Distal layer 280, in this implementation, is formed, at least in part, of silicone 235. Fenestrations 260 disposed about distal layer 280 are illustrated as either square or star-burst shaped, and fenestrations 260 allow the communication of exudate 218, material 216, or both exudate 218 and material 216 between distal side 282 and proximal side 284 of distal layer 280, as illustrated.

As illustrated in FIG. 3, window 227 formed of transparent or translucent material is disposed in structural member 220 between proximal side 224 and distal side 222. For example, window 227 may be formed of a polypropylene or polyethylene film that is sealed against a linear aperture within layer 220. A user may view at least portions of pad 270, for example, to determine a degree of saturation of pad 270 by exudate, such as exudate 218. As another example, an indicator, such as indicator 178, may be included in pad 270, and the indicator may be viewed through window 227, the indicator being indicative of the pH of pad 270, and, thus, indicative of conditions of wound bed 213.

Figure 4:
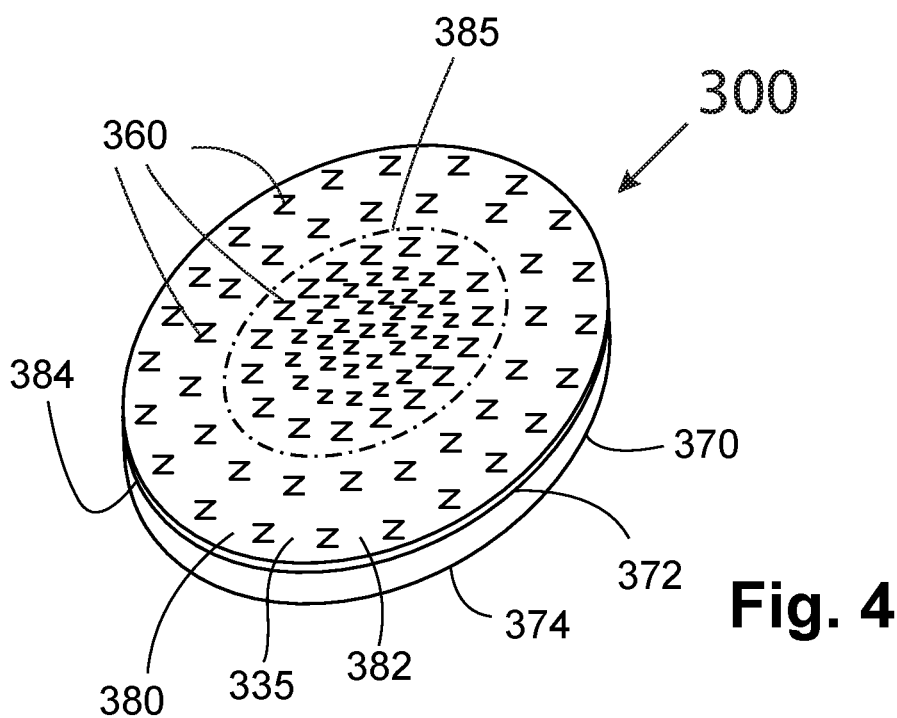
FIG. 4 illustrates by perspective view at least portions of a third exemplary implementation of a wound therapy apparatus.

FIG. 4 illustrates distal layer 380 and pad 370 of exemplary wound therapy apparatus 300. Pad 370 conforms in shape to distal layer 380 with both pad 370 and distal layer 380 being circular in shape, in this implementation. Pad 370 has distal side 372 and proximal side 374, and distal side 372 of pad 370 is secured to proximal side 384 of distal layer 380, as illustrated. Distal layer 380 is formed, at least in part, of silicone 335, and pad 370 may be formed of materials similar to those of pad 170 of exemplary wound therapy apparatus 100, in this implementation. Fenestrations 360 disposed about distal layer 380 pass between distal side 382 and proximal side 384 of distal layer 380, in this implementation. As illustrated in FIG. 4, the fenestrations 360 are formed as Z-shaped slits. Note that fenestrations 360 decrease in size and increase in concentration within a central region of distal layer 380 within boundary 385 while fenestrations 360 are regularly sized and distributed outside boundary 385, as illustrated in FIG. 4.

Figure 5:
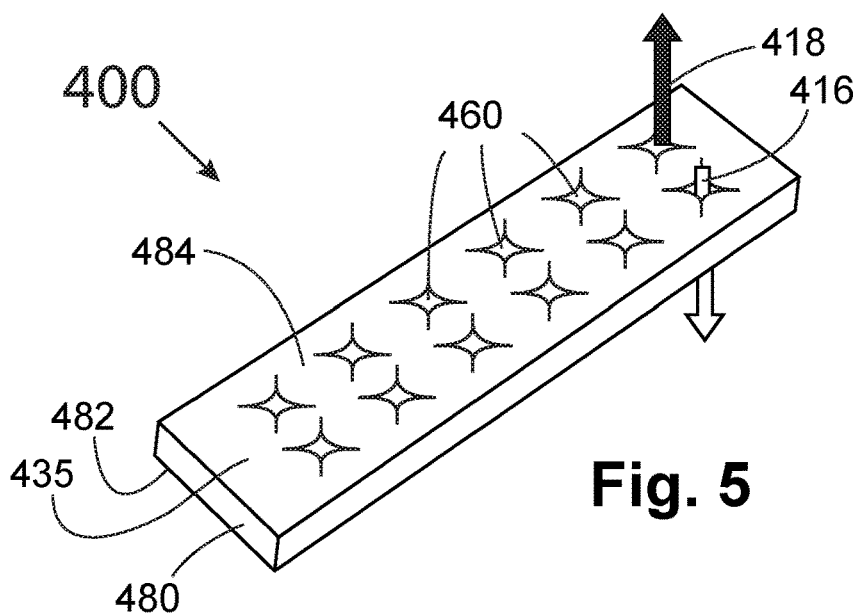
FIG. 5 illustrates by perspective view at least portions of a fourth exemplary implementation of a wound therapy apparatus.

FIG. 5 illustrates distal layer 480, which is formed, at least in part, of silicone 435, in exemplary wound therapy apparatus 400, and distal layer 480 including fenestrations 460 that pass between distal side 482 and proximal side 484 of distal layer 480 to allow communication of material 416 and exudate 418 between distal side 482 and proximal side 484. In FIG. 5, distal layer 480 has an elongated rectangular shape, and fenestrations 460 are formed as star-burst shaped slits passing between distal side 482 and proximal side 484 of distal layer 480.

Figure 6A:
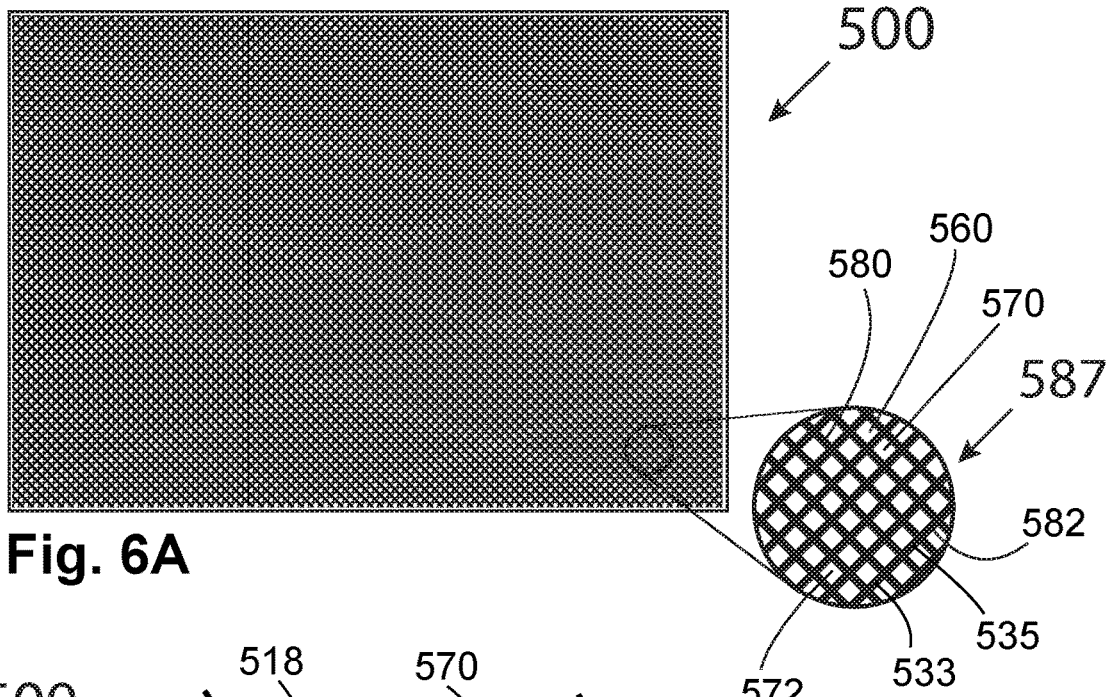
FIG. 6A illustrates by plan view at least portions of a fifth exemplary implementation of a wound therapy apparatus.
Figure 6B:
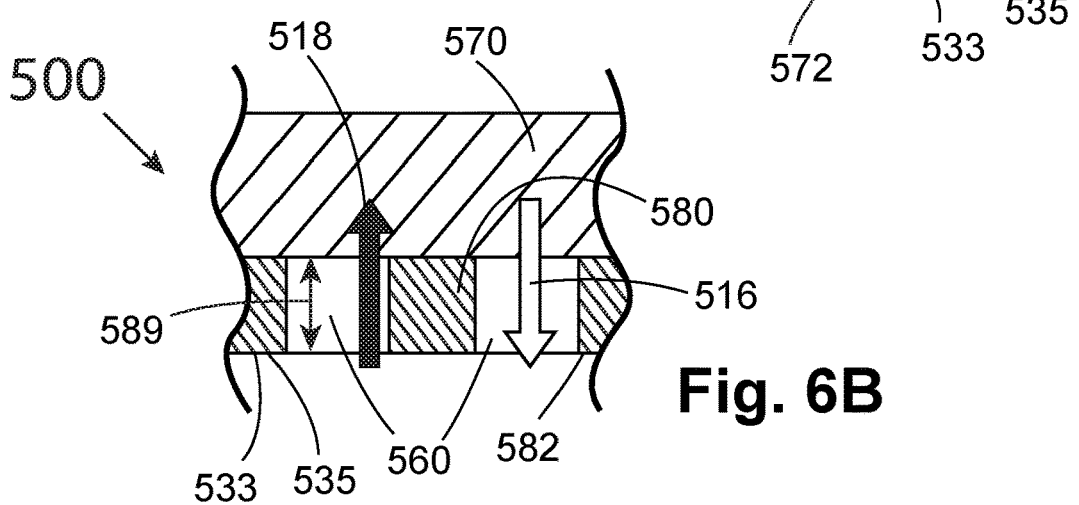
FIG. 6B illustrates by cross-sectional view portions of the fifth exemplary implementation of a wound therapy apparatus of FIG. 6A.

FIGS. 6A, 6B illustrate exemplary wound therapy apparatus 500 including distal layer 580 formed, at least in part, of silicone 535 and pad 570. As illustrated in FIG. 6A, distal layer 580 is formed over the distal side 572 of pad 570, and distal layer 580 does not occlude the entire distal side 572 of pad 570. Distal layer 580 may be formed, for example, by rolling, spraying, or otherwise applying a layer of silicone material in pattern 587 over the distal side 572 of the pad 570 during manufacture. Various stencils, masks, screens, and so forth may be used to form pattern 587.

The silicone material may be, for example, silicone gel that may include one or more polysiloxanes, silicone dioxide, and a carrier formed of a volatile solvent, in various implementations. An example of a silicone gel is a dispersion of polysilicone-11 in phenyltrimethicone as carrier. Following application of the silicone gel to the distal side 572 of pad 570, the carrier, such as phenyltrimethicone, evaporates leaving the silicone 535 in place on distal side 572 of the pad 570 as distal layer 580 with pattern 587. The combined pad 570 and distal layer 580 then be die-cut and then assembled on the distal side of a structural member, such as structural member 120, 620, 720.

FIG. 6A illustrates distal side 582 of distal layer 580. As illustrated in the detail of FIG. 6A, distal layer 580 is formed, at least in part, of silicone 535 with pattern 587, and pad 570 may be formed of materials similar to those of pad 170 of exemplary wound therapy apparatus 100. While pattern 587 is illustrated as generally of a regular rectangular geometry, pattern 587 may have various shapes, combinations of regularity and irregularity, and size distributions, in other implementations. Pattern 587 of distal layer 580 defines occluded regions 533 with fenestrations 560 between occluded regions 533 that expose distal side 572 of pad 570 to allow communication of exudate 518 or material 516 between distal side 582 and proximal side 584 of distal layer 580 and with distal side 572 of pad 570, as illustrated in FIGS. 6A, 6B. Thickness 589 of distal layer 580 may range from about 200 microns to about 1000 microns, in various implementations. Fenestrations 560 may range from about 50 microns (#270 Mesh) to about 1000 microns (#18 Mesh) in diameter or equivalent, or from about 100 microns (#140 Mesh) to about 750 microns (about #22 Mesh) in diameter or equivalent. The number of fenestrations 560 per $cm^2$ may generally range from about 45 per $cm^2$ to about 2500 per $cm^2$, in various implementations.

Figure 7A:
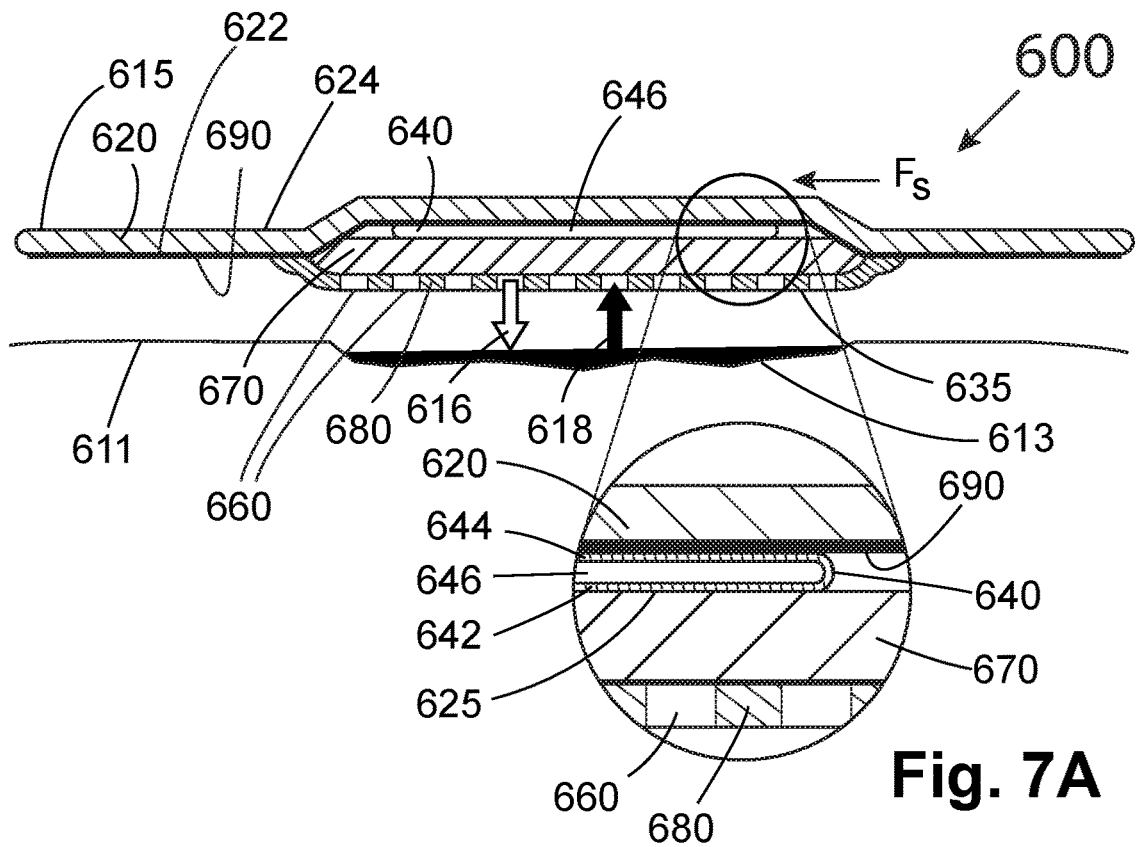
FIG. 7A illustrates by cross-sectional view a sixth exemplary implementation of a wound therapy apparatus.

FIG. 7A illustrates wound interface 615 of exemplary wound therapy apparatus 600 set apart from wound bed 613 and skin surface 611 for purposes of clarity of explanation. Wound bed 613 includes skin graft 615, in this implementation. Wound interface 615 includes distal layer 680 and pad 670 in cooperation with structural member 620 with pad 670 interposed between distal layer 680 and structural member 620. Distal layer 680 is formed, at least in part, of silicone 635, in this implementation. Adhesive 690 disposed about structural member 620 may affix structural member 620, and, thus, wound interface 615 to skin surface 611 to bias distal layer 680 against wound bed 613, in this implementation. Exudate 618 may be communicated through fenestrations 660 in proximal layer from wound bed 613 to pad 670, and material 616 may be communicated from pad 670 through fenestrations 660 to wound bed 613, as illustrated.

Shear force $F_s$, is illustrated in FIG. 7A as acting tangentially upon wound interface 615 of wound therapy apparatus 600. Shear force $F_s$, may arise from various impacts having a tangential component upon wound interface 615 as may be incurred during the course of wearing of wound interface 615, for example, due to bumping on objects and interactions with clothing or bedding.

In the implementation of FIG. 7A, wound interface 615 includes spacer 640 having an envelope-like construction and located between adhesive 690, which is disposed over distal side 622 of structural member 620, and pad 670. In other implementations, spacer 640 may be located between structural member 620 and adhesive 690. Spacer 640 includes distal layer 642 and proximal layer 644, and distal layer 642 and proximal layer 644 define space 646 in between, as illustrated. Spacer 640 may be formed as a film of a low-friction material 625 such as polyethylene or polypropylene for slideable engagement of proximal layer 644 with distal layer 642. The slideable engagement of proximal layer 644 with distal layer 642 in spacer 640 may at least partially deflect shear force $F_s$, to reduce the transmission of shear force $F_s$, to distal layer 680, and thence to wound bed 613. Proximal side 624 of structural member 620 may be formed of low friction material 625 in order to deflect shear force $F_s$, for example, to allow slippage between proximal side 624 and objects that contact proximal side 624. Accordingly, shear reducing means for reducing the transmission of shear force $F_s$, to wound bed 613 may include spacer 640 having proximal layer 644 and distal layer 642 with space 646 therebetween, and the shear reducing means may include proximal side 624 of structural member 620 formed of low friction material 625.

Ab initio, the skin graft 615 is devoid of vascular connection. After a period of time, neovascular twigs begin to appear, reaching from the wound bed towards the skin graft 615 and ultimately establishing blood flow and viability of the graft. If the wound bed 613 including skin graft 615 is sheared during the vascularization period, the viability of the skin graft 615 is threatened. Thus, inclusion of spacer 640 or a low friction material 625 in proximal side 624 of structural member 620 may protect wound bed 613 including skin graft from disruption by shear force $F_s$, by reducing of the transmission of shear force $F_s$, to wound bed 613 or deflecting shear force $F_s$, respectively.

Figure 7B:
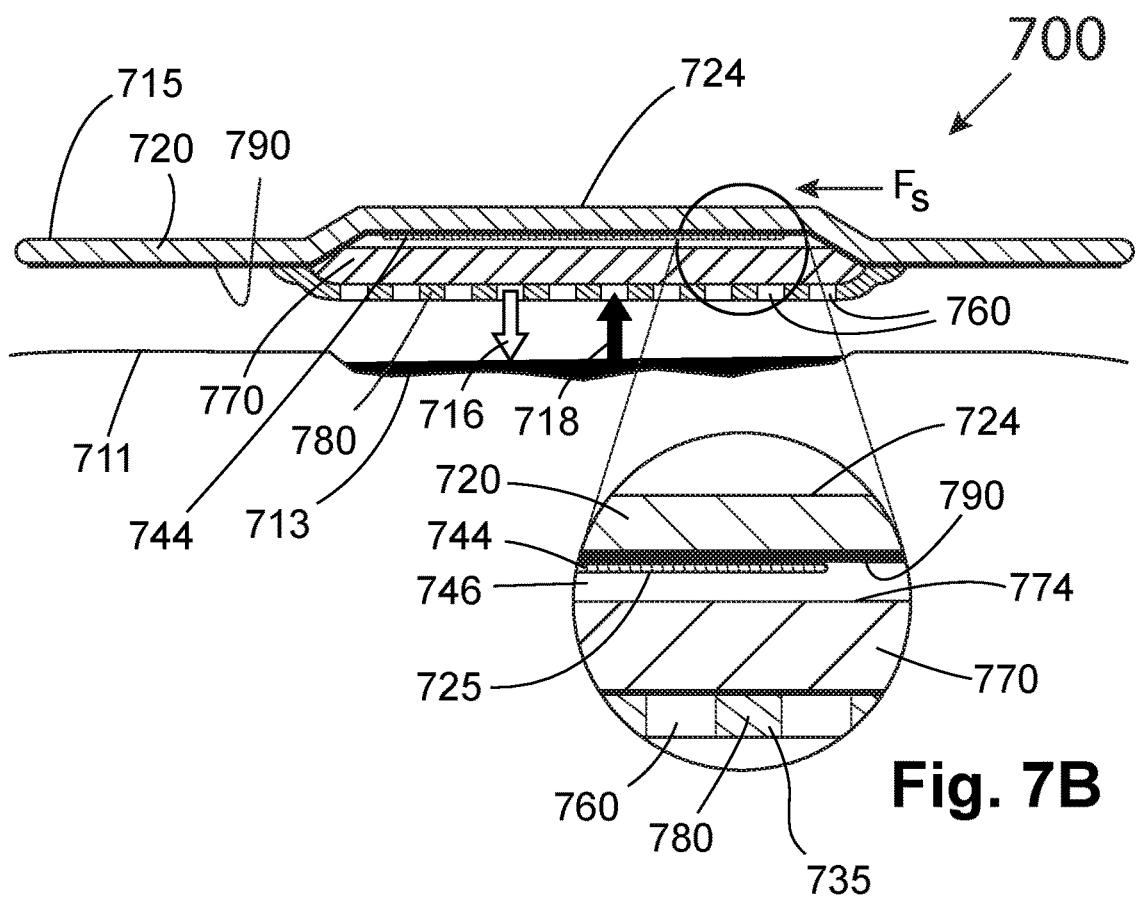
FIG. 7B illustrates by cross-sectional view a seventh exemplary implementation of a wound therapy apparatus; and, FIG. 8 illustrates by perspective view at least portions of an eighth exemplary implementation of a wound therapy apparatus.

FIG. 7B illustrates wound interface 715 of exemplary wound therapy apparatus 600 including pad 770 interposed between distal layer 780 and structural member 720. Wound interface 715 is illustrated as set apart from wound bed 713 and skin surface 711 for clarity of explanation. Distal layer 780 is formed, at least in part, of silicone 735, and distal layer 780 includes fenestrations 760 for the communication of exudate 718 and material 716 therethrough. Layer 742 is interposed between adhesive layer 790 and proximal side 774 of pad 770 with space 746 between layer 742 and proximal side 774 of pad 770, as illustrated. Layer 742 may be formed as a film of a low-friction material 725 such as polyethylene or polypropylene to facilitate slideable engagement between layer 742 and proximal side 774 of pad 770 that may reduce the transmission of shear force $F_s$ applied to proximal side 724 of structural member to distal layer 780. As illustrated, layer 742 prevents adhesion of at least portions of pad 770 to structural member 720 by adhesive 790, and slideable engagement of layer 742 with proximal side 774 of pad allows movement between portions of structural member 720 and pad 770 to at least partially deflect shear force $F_s$ applied to proximal side 724 of structural member 720. This may reduce the transmission of shear force $F_s$ to wound bed 713. In other implementations, for example, adhesive 790 may be omitted from portions of structural member 790 proximate proximal side 774 of pad 770 and layer 742 may be omitted so that at least portions of proximate proximal side 774 of pad 770 are slideably engaged with structural member 720 to allow movement between portions of structural member 720 and pad 770 that may least partially deflect shear force $F_s$ applied to proximal side 724 of structural member 720. Accordingly, shear reducing means for reducing the transmission of shear force $F_s$ to wound bed 713 may include, for example, layer 742 with space 746.

Figure 8:
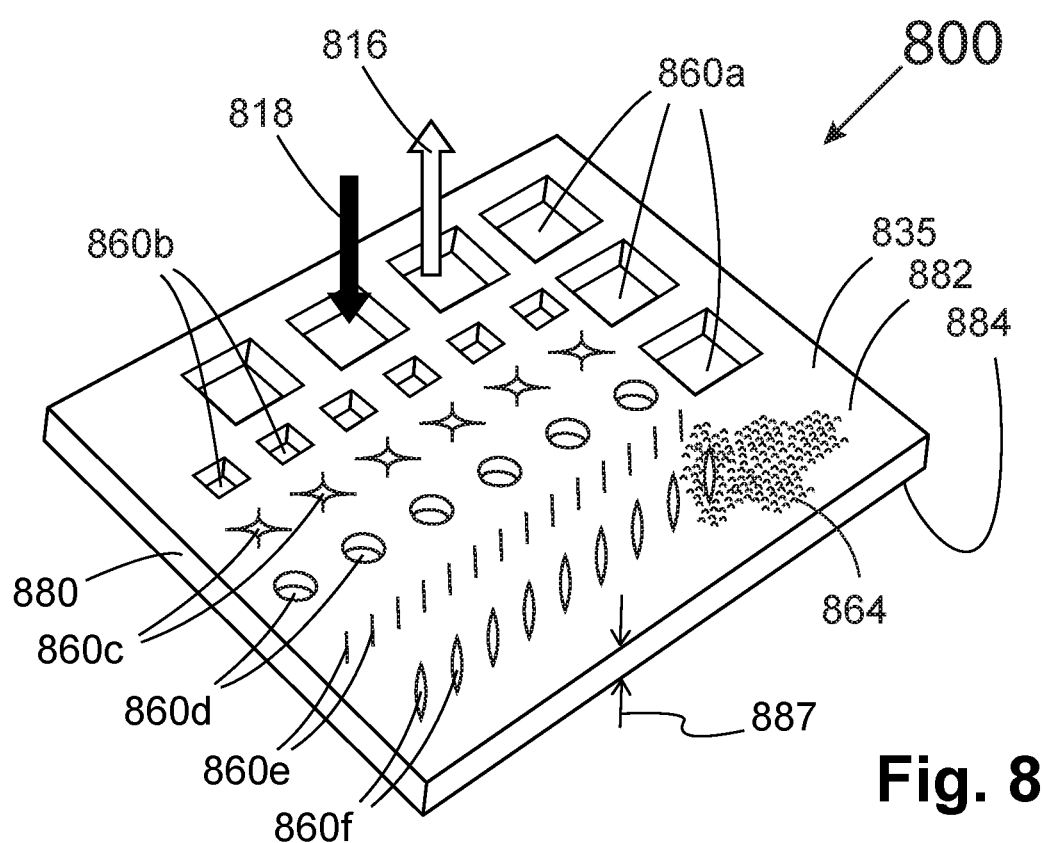

FIG. 8 illustrates distal layer 880 of exemplary wound therapy apparatus 800, and distal layer 880 is formed, at least in part, of silicone 835. As illustrated in FIG. 8, the fenestrations 860a, 860b, 860c, 860d, 860e, 860f passing between distal side 882 and proximal side 884 have a square, rectangular, starburst, circular, slit, and fish-mouthed geometries, respectively, and may be disposed about distal layer 880 in various fenestration patterns. Exudate 818 or material 816 may be communicated through fenestrations 860a, 860b, 860c, 860d, 860e, 860f between distal side 882 and proximal side 884. Geometry of fenestrations, such as fenestrations 860a, 860b, 860c, 860d, 860e, 860f, and fenestration patterns may be selected to preserve patency of the fenestrations during use that allows communication of exudate 818 or material 816 through the fenestrations. For example, fenestrations that are Z-shaped (e.g., fenestrations 360 in FIG. 4) may be more likely to remain functionally patent than simple slits because the Z-shape may allow for more multidirectional stretching of the distal layer. Fish-mouthed fenestrations, such as fenestrations 860f, may also exhibit increased patency.

FIG. 8 illustrates texture 864 on distal surface 882 of distal layer 880 that may be micro- or macro-surface textures in the form, for example, of bumps, pits, ridges, and combinations thereof. Texture 864 when biased against a wound bed, such as wound bed 113, 213, 613, 713 may cause micro-deformation and pressure points that may accelerate wound healing by stimulating cellular mitosis, differentiation, and angiogenesis.

As illustrated herein, the wound therapy apparatus, in some implementations, may include a distal layer, such as distal layer 180, 280, 680, 780, a pad, such as pad 170, 270, 670, 770, and a structural member, such as structural member 120, 220, 620, 720, as in wound therapy apparatus 100, 200, 600, 700. The wound therapy apparatus, in other implementations, may include a distal layer, such as distal layer 380, 580, and a pad, such as pad 370, 570, as in wound therapy apparatus 300, 500. The wound therapy apparatus, in yet other implementations, may include a distal layer, such as distal layer 480, as in wound therapy apparatus 400.

In various exemplary methods of operation, for example, a distal layer, such as distal layer 180, 280, 380, 480, 580, 680, 780, 880 of a wound therapy apparatus, such as wound therapy apparatus 100, 200, 300, 400, 500, 600, 700, 800 may be contacted with a wound bed, such as wound bed 113, 213, 613, for example, shortly after injury and before scar formation takes place. The distal layer, which is formed, at least in part, of silicone, such as silicone 135, 235, 335, 435, 535, 635, 735, 835, may provide an early homeostatic influence and may balance the collagen, fibronectin and collagenase levels in order to promote healing and reduce scarring that may obviate the protracted need for reversing excessive scarring after a scar had already formed.

In one exemplary method of operation, for example, the wound bed, which is unhealed, is contacted with the distal layer, which is formed, at least in part, of silicone, and the distal layer is employed essentially by itself with the pad, such as pad 170, 270, 370, 470, 570, 670, 770 and the structural member, such as structural member 120, 200, 620, 720 being omitted.

In another exemplary method of operation, the wound bed is contacted with the distal layer, and the distal layer is engaged with the pad, the structural member being omitted. In such exemplary methods of operation, the pad absorbs exudate, such as exudate 118, 218, 418, 518, 618, 818, communicated to the pad from the wound bed through fenestrations, such as fenestration 160, 260, 360, 460, 560, 660, 760, 860a, 860b, 860c, 860d, 860e, 860f, in the distal layer. Material, such as material 116, 216, 416, 516, 616, 816, may be communicated to the wound bed through the fenestrations.

In a third exemplary method of operation, the wound bed is contacted with the distal layer, and the distal layer is engaged with the pad, and the structural member is deployed to cover the structure, such as structure 150, that includes the combination of distal layer with pad. The structural member may protect the pad, the distal member, or the pad in combination with the distal member, and the structural member may protect the wound bed.

In methods of operation that include the pad, the distal layer and the pad may be removed and then discarded when indicated, for example, when the pad is at least partly saturated with exudate. In some operations, a wound interface, such as wound interface 115, 215, 615, 715 may be removed and replaced with another wound interface that may be either similar to or dissimilar from the wound interface that was removed. Different wound interfaces may be used during the course of treatment of the wound bed, for example, as the amount of exudate exuded by the wound bed decreases or to deliver various medicaments, such as medicament 176, to the wound bed.

Various methods of operation may include delivery of the medicament to the wound bed through the distal layer from the pad. Various methods of operation may include contacting the wound bed with texture, such as texture 864, disposed about the distal side of the distal layer that may accelerate healing of the wound bed or may aid in apposition of the wound bed. Various methods of operation may include observing the pad through a window, such as window 227, disposed about the structural member. Various methods of operation may include observing an indicator, such as indicator 178, included in the pad, and the indicator may be observed through the window. Various methods of operation may include decreasing the shear force $F_s$ transmitted though the wound interface to the wound bed. Various methods of operation may include removing exudate or fluid from the wound interface via one or more ports disposed about the wound interface, and may include inputting fluid into the wound interface via one or more ports disposed about the wound interface.

The foregoing discussion along with the Figures discloses and describes various exemplary implementations. These implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations can be made thereto without departing from the spirit and scope of the inventions as defined in the following claims.

What is claimed is:

1. A wound therapy apparatus, comprising:
 a pad; and
 a distal layer formed as a coating of a silicone material only on a distal surface of the pad that is non-occlusive in part to communicate exudate from a wound bed through non-occluded portions of the distal surface of the pad into the pad, the non-occluded portions defining fenestrations that pass only through the silicone material between a distal side of the distal layer and a proximal side of the distal layer.

2. The apparatus of claim 1, further comprising:
 a structural member engaged with the pad, the structural member adhesively securable to a skin surface about the wound bed to hold a distal side of the distal layer in contact with the wound bed.

3. The apparatus of claim 1, wherein the silicone material comprises a combination of one or more polysiloxanes and a carrier.

4. The apparatus of claim 2, wherein at least a portion of the structural member is formed of a material selected from a group consisting of a transparent material and a translucent material.

5. The apparatus of claim 2, further comprising:
 a film disposed between the structural member and the distal layer configured to deflect at least a portion of a shear force applied externally to the structural member.

6. The apparatus of claim 2, wherein the structural member is configured to form an occlusive space over the wound bed upon adhesive securement to the skin surface about the wound bed.

7. The apparatus of claim 2, wherein the structural member is configured to allow passage therethrough of a material selected from a group consisting of $O_2$, $CO_2$, and water vapor.

8. The apparatus of claim 2, further comprising:
 an adhesive disposed on the structural member.

9. The apparatus of claim 1, further comprising:
 a medicament disposed within the pad.

10. The apparatus of claim 1, wherein the pad comprises a combination of a hydrophobic material and a hydrophilic material.

11. The apparatus of claim 10, wherein the pad distal surface is comprised of more of the hydrophobic material than of the hydrophilic material and a pad proximal surface of the pad is comprised of more of the hydrophilic material than of the hydrophobic material.

12. The apparatus of claim 1, wherein the fenestrations have a diameter within a range of 50 microns to 1000 microns.

13. The apparatus of claim 1, wherein a concentration of the fenestrations is within a range of from 45 fenestration per square centimeter to 2500 fenestrations per square centimeter.

14. The apparatus of claim 13, wherein the concentration of the fenestrations varies in differing portions of the distal layer.

15. The apparatus of claim 1, wherein the distal layer has a thickness within a range of 200 microns to 1000 microns.

16. The apparatus of claim 1, wherein the silicone material comprises a polysiloxane.

17. The apparatus of claim 1, wherein the silicone material comprises a polysiloxane dispersed in a solvent.

18. The apparatus of claim 1, wherein the silicone material comprises a silicone polymer having a molecular weight in a range between $10^5$ and $10^7$.

19. The apparatus of claim 1, wherein a combination of the distal layer disposed upon the pad is die cut.

20. The apparatus of claim 1, wherein the distal layer is formed by spraying the silicone material onto the distal surface of the pad.

* * * * *